United States Patent
Stanaford et al.

(10) Patent No.: US 8,821,554 B2
(45) Date of Patent: Sep. 2, 2014

(54) METHOD, SYSTEM, AND APPARATUS FOR MAMMALIAN BONY SEGMENT STABILIZATION

(75) Inventors: Todd Stanaford, Midland, TX (US); Leonel Dominguez, Jacksonville, FL (US)

(73) Assignee: Amendia, Inc., Marietta, GA (US)

( * ) Notice: Subject to any disclaimer, the term of this patent is extended or adjusted under 35 U.S.C. 154(b) by 71 days.

(21) Appl. No.: 12/826,665

(22) Filed: Jun. 29, 2010

(65) Prior Publication Data

US 2011/0319893 A1 Dec. 29, 2011

Related U.S. Application Data

(63) Continuation-in-part of application No. 12/268,402, filed on Nov. 10, 2008, now abandoned.

(51) Int. Cl.
*A61B 17/80* (2006.01)
*A61B 17/70* (2006.01)

(52) U.S. Cl.
CPC ......... *A61B 17/7059* (2013.01); *A61B 17/8061* (2013.01); *A61B 17/8042* (2013.01)
USPC .......................................... 606/295; 606/294

(58) Field of Classification Search
CPC .................................................. A61B 17/8042
USPC ................................................. 606/295, 294
See application file for complete search history.

(56) References Cited

U.S. PATENT DOCUMENTS

| | | | |
|---|---|---|---|
| 6,258,089 B1 | 7/2001 | Campbell et al. | |
| 6,413,259 B1 | 7/2002 | Lyons et al. | |
| 6,602,255 B1* | 8/2003 | Campbell et al. | 606/290 |
| 6,626,907 B2 | 9/2003 | Campbell et al. | |
| 7,273,481 B2 | 9/2007 | Lombardo et al. | |
| 2004/0133205 A1 | 7/2004 | Thramann et al. | |
| 2005/0010227 A1 | 1/2005 | Paul | |
| 2005/0059971 A1* | 3/2005 | Michelson | 606/69 |
| 2005/0137597 A1 | 6/2005 | Butler et al. | |
| 2005/0149027 A1 | 7/2005 | Campbell et al. | |
| 2005/0251138 A1 | 11/2005 | Boris et al. | |
| 2005/0283152 A1* | 12/2005 | Lindemann et al. | 606/61 |
| 2006/0015104 A1* | 1/2006 | Dalton | 606/70 |
| 2008/0287999 A1* | 11/2008 | Markworth | 606/280 |
| 2009/0192553 A1* | 7/2009 | Maguire et al. | 606/305 |
| 2010/0121383 A1* | 5/2010 | Stanaford et al. | 606/280 |

FOREIGN PATENT DOCUMENTS

| | | | |
|---|---|---|---|
| WO | 2005006997 A1 | 1/2005 | |
| WO | 2006104487 A1 | 5/2006 | |
| WO | 2006119242 A1 | 11/2006 | |
| WO | 2008005380 A2 | 1/2008 | |

\* cited by examiner

*Primary Examiner* — David Bates
(74) *Attorney, Agent, or Firm* — David L. King

(57) ABSTRACT

Embodiments of bony region stabilization are described generally herein. Other embodiments may be described and claimed.

5 Claims, 21 Drawing Sheets

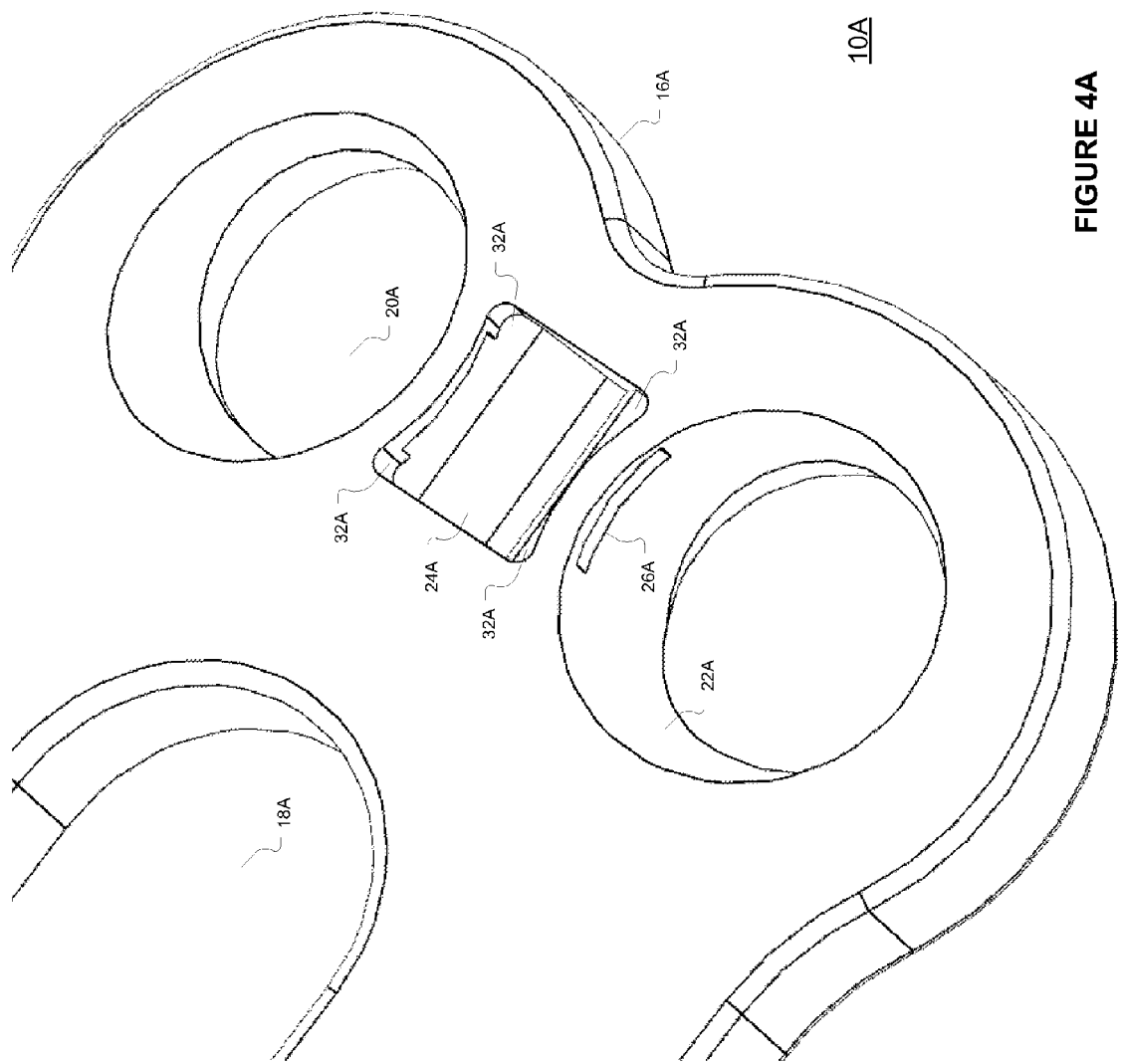

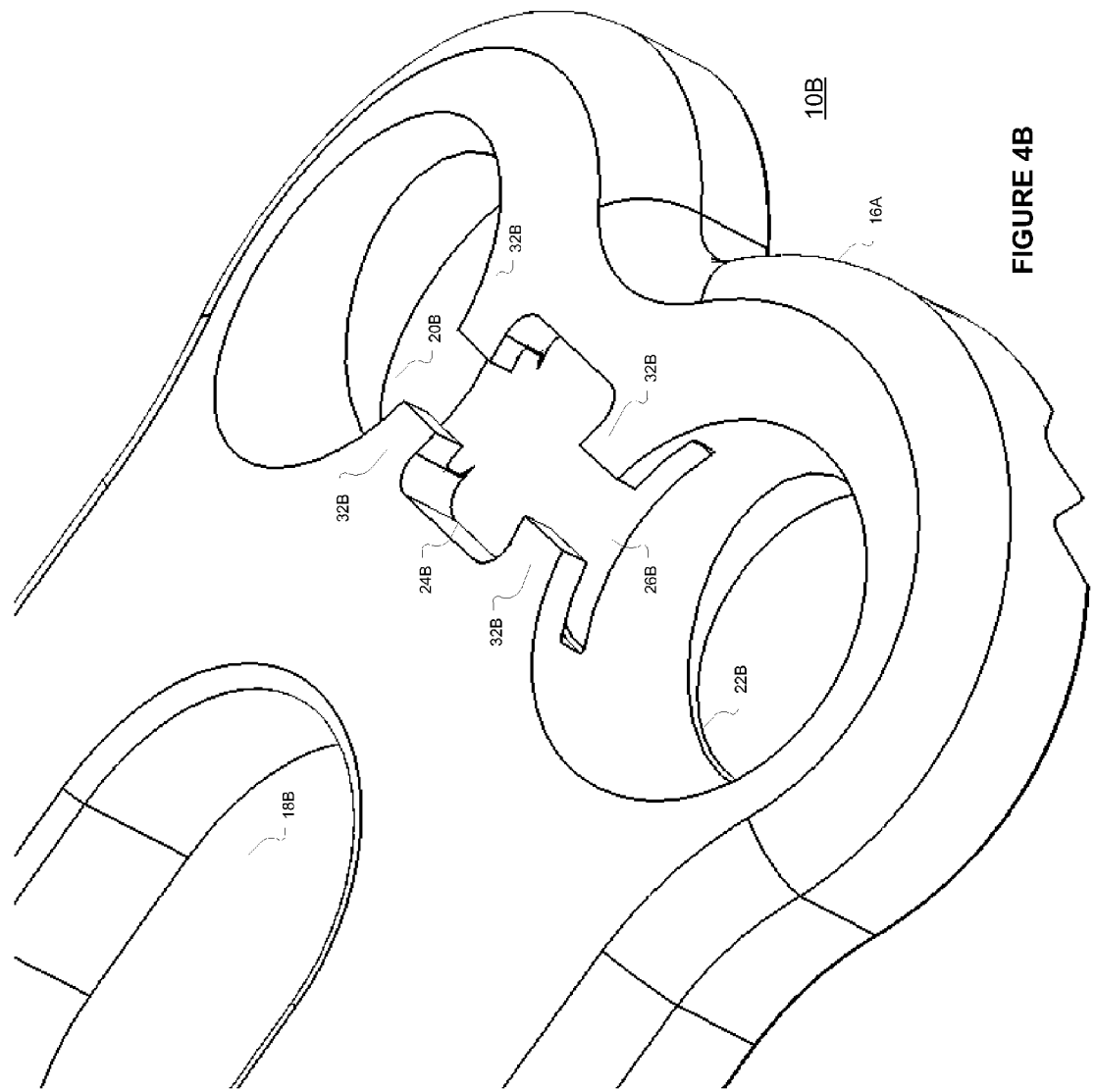

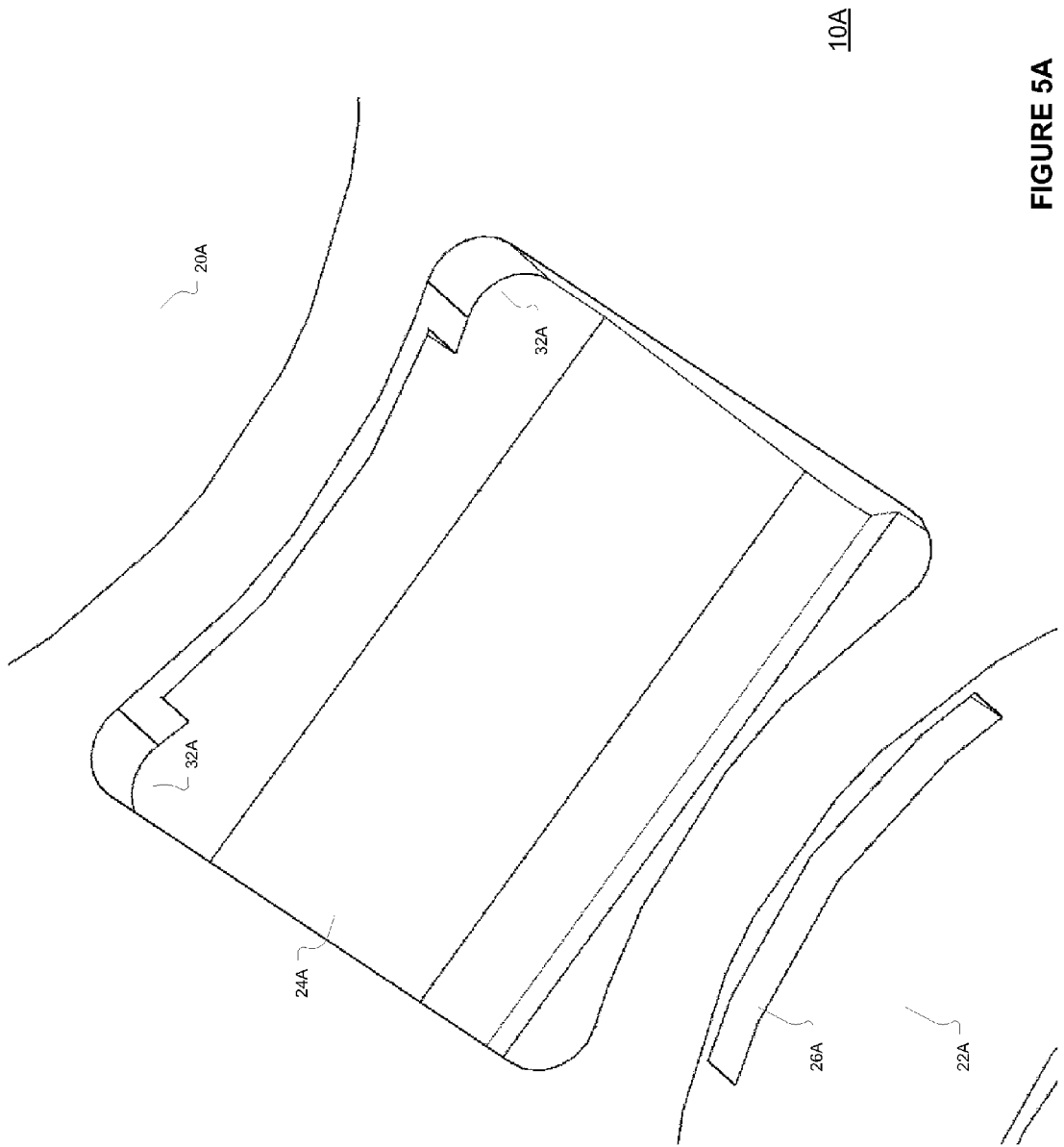

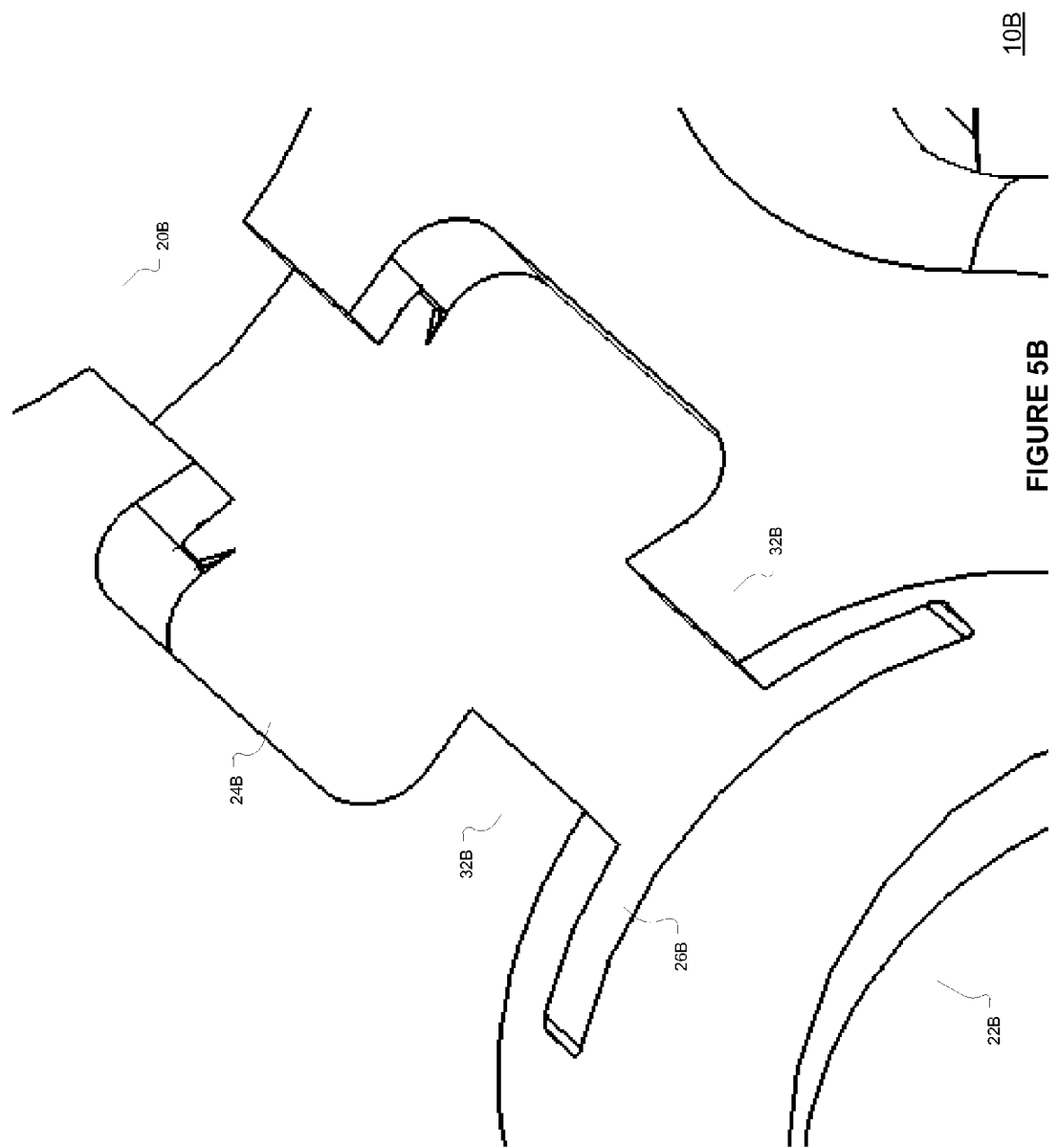

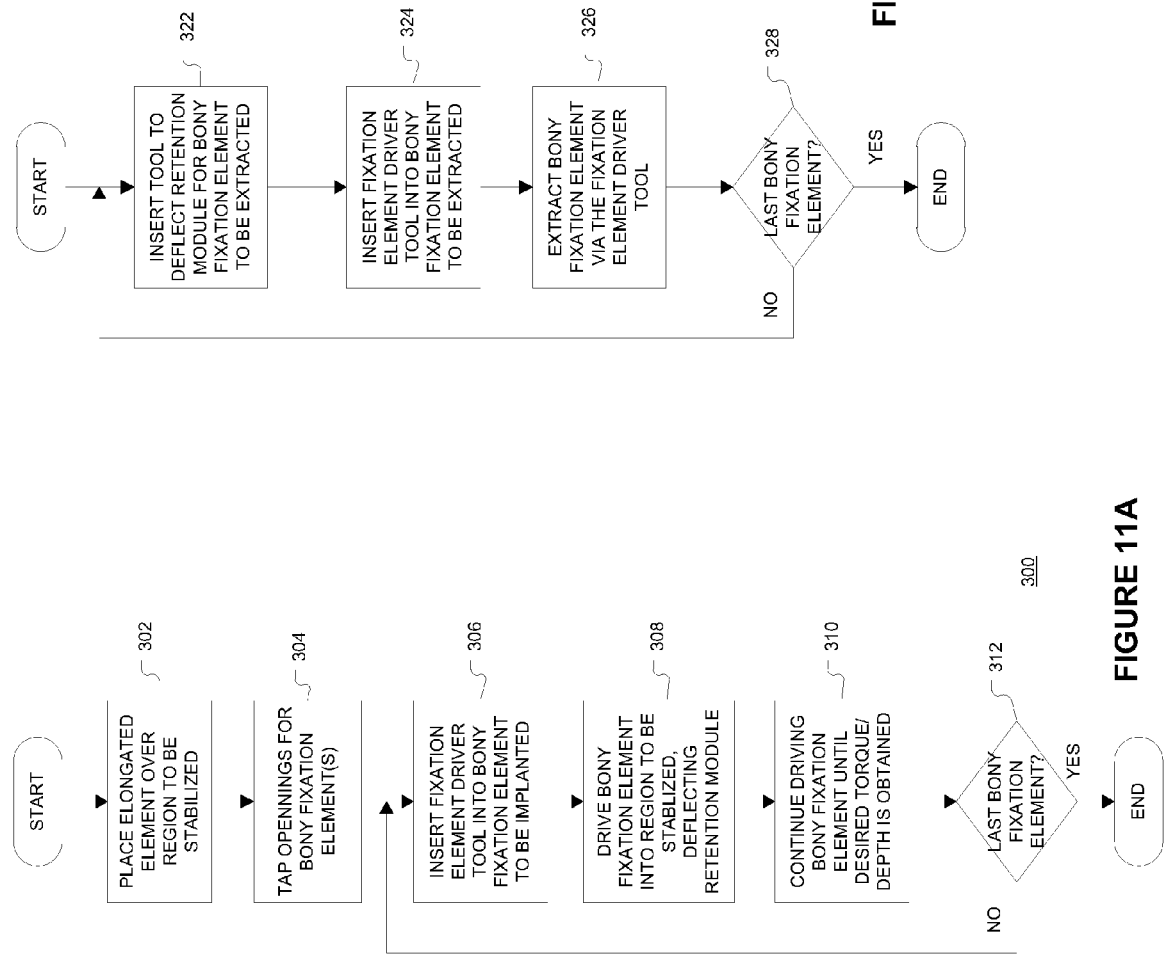

METHOD, SYSTEM, AND APPARATUS FOR MAMMALIAN BONY SEGMENT STABILIZATION

CROSS REFERENCE TO RELATED APPLICATIONS

The present application is a continuation in part of, now abandoned, application Ser. No. 12/268,402, entitled "METHOD, SYSTEM, AND APPARATUS FOR MAMMALIAN BONY SEGMENT STABILIZATION", filed Nov. 10, 2008, which is incorporated herein by reference.

TECHNICAL FIELD

Various embodiments described herein relate generally to stabilizing mammalian bony segments, including systems and methods employing an elongated element to stabilize one or more mammalian bony segments.

Background Information

It may be desirable to stabilize one or more bony segments via an elongated element, the present invention provides such treatment.

BRIEF DESCRIPTION OF THE DRAWINGS

FIG. 4A is a simplified, isometric front, partial view of a mammalian bony segment stabilization system elongated element bony fixation element coupling segment according to various embodiments.

FIG. 4B is a simplified, isometric front, partial view of a mammalian bony segment stabilization system elongated element bony fixation element coupling segment according to various embodiments.

FIG. 5A is a simplified, isometric front, partial view of a mammalian bony segment stabilization system elongated element bony fixation element retention module cavity according to various embodiments.

FIG. 5B is a simplified, isometric front, partial view of a mammalian bony segment stabilization system elongated element bony fixation element retention module cavity according to various embodiments.

FIG. 11A-11B are flow diagrams illustrating mammalian bony segment stabilization processing algorithms according to various embodiments.

DETAILED DESCRIPTION

Figure 1B:
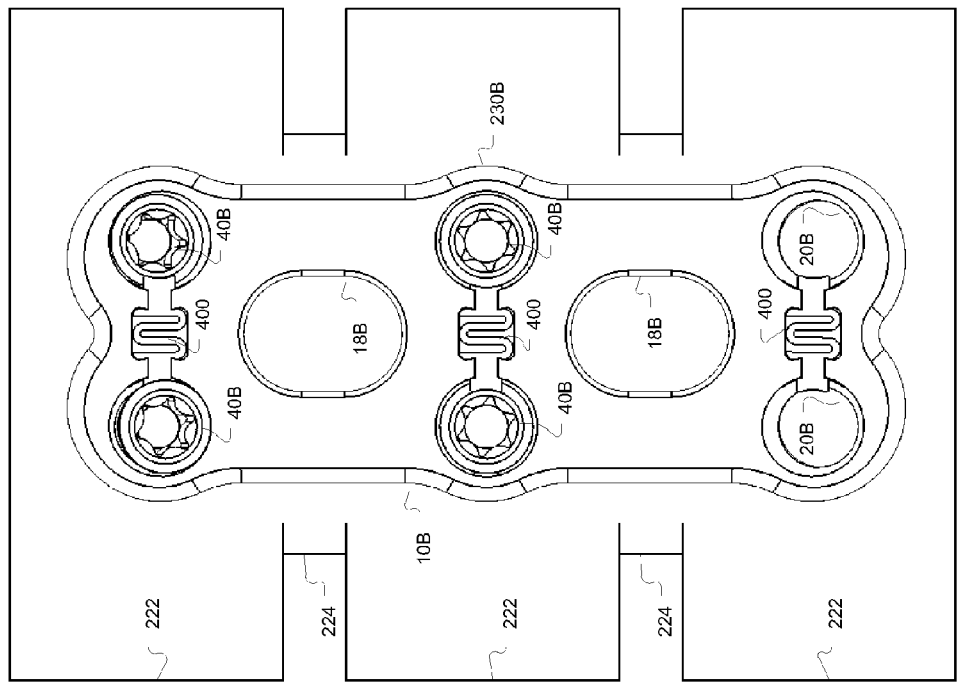
FIG. 1B is a simplified diagram of mammalian bony segment stabilization architecture according to various embodiments.
Figure 1A:
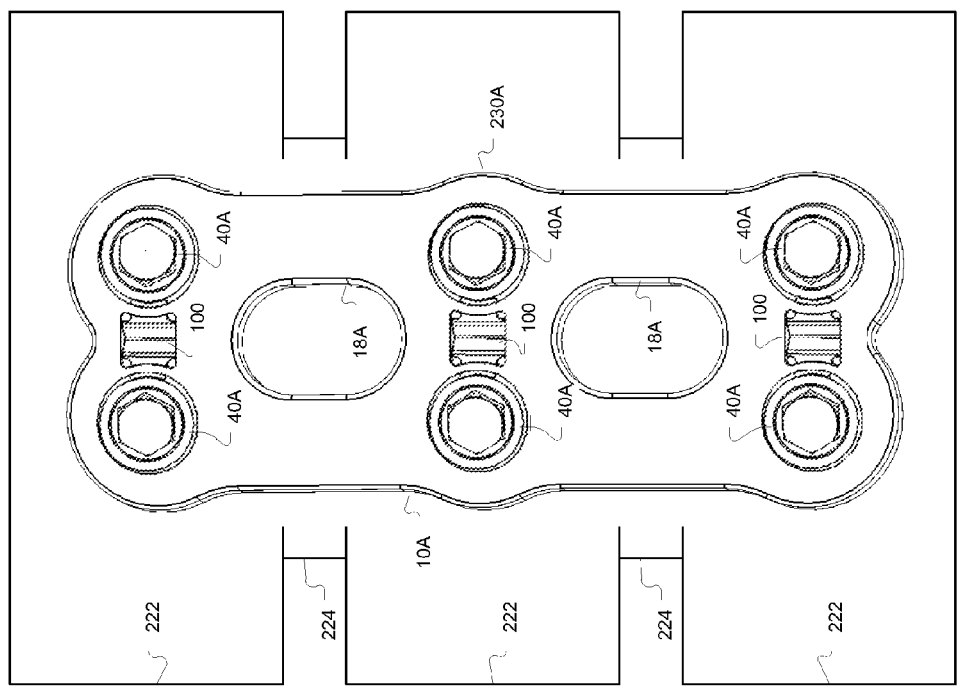
FIG. 1A is a simplified diagram of mammalian bony segment stabilization architecture according to various embodiments.

FIGS. 1A and 1B are simplified diagrams of mammalian bony segment stabilization architecture 220A, 220B according to various embodiments. The architecture 220A includes a mammalian bony segment stabilization system 230A coupled to a plurality of bony regions 222. The bony segment stabilization system 230A includes an elongated element 10A extending to at least two or more bony regions 222 to be stabilized. The elongated element 10A may include at least one opening (20A in FIG. 2A) adjacent or within the two or more bony regions 222. The elongated element 10A may be fixably coupled to each bony region 222 via the opening 20A and bony coupling elements 40A such as a screw, pin, or other bony region coupling or fixation element.

In the embodiment 230A the elongated element 10A includes openings 20A that may accommodate at least one bony fixation element 40A. The system 230A may couple multiple bony regions 222. In an embodiment the element 10A may include six openings 20A for up to six corresponding spinal fixation elements 40A. An elongated element 10A may also include one or more openings 18A that may enable a user to insert or visualize implants in the region 224 and visually inspect the region 224. The implants may be comprised of any biocompatible material including bone, polymers, and metals. Further the elongated element 10A may be comprised of any biocompatible material including bone, polymers, and metals.

In an embodiment, the bony segment stabilization system 230A further includes at least one bony fixation element retention module 100. The bony fixation element retention module 100 may engage a bony fixation element 40A via a slot or channel 26A in an opening 20A (FIG. 4A). The bony fixation element retention module 100 may include at least one arm 106 (FIG. 6A) where the arm 106 may limit or prevent bony fixation element 40A dislocation from a bony region 222 and may limit or prevent bony fixation element 40A projection beyond a front surface 28A (FIG. 2A) of the elongated element 10A.

In an embodiment one or more bony regions 222 may be separated by one or more non-bony elements 224, for example bony regions 222 may be vertebra separated by spinal discs 224 in a cervical, thoracic, or lumbar region of a mammal including a human. In another embodiment the bony regions 222 may be part of a single, fractured bone to be stabilized such a femur or other long mammalian bone.

The architecture 220B includes a mammalian bony segment stabilization system 230A coupled to a plurality of bony regions 222. The bony segment stabilization system 230B includes an elongated element 10B extending to at least two or more bony regions 222 to be stabilized. The elongated element 10B may include at least one opening (20B in FIG. 2B) adjacent or within the two or more bony regions 222. The elongated element 10B may be fixably coupled to each bony region 222 via the opening 20B and bony coupling elements 40B such as a screw, pin, or other bony region coupling or fixation element.

In the embodiment 230B the elongated element 10B includes openings 20B that may accommodate at least one bony fixation element 40B. The system 230B may couple multiple bony regions 222. In an embodiment, the element 10B may include six openings 20B for up to six corresponding spinal fixation elements 40B. An elongated element 10B may also include one or more openings 18B that may enable a user to insert or visualize implants in the region 224 and visually inspect the region 224. The implants may be comprised of any biocompatible material including bone, polymers, and metals. Further the elongated element 10B may be comprised of any biocompatible material including bone, polymers, and metals.

In an embodiment, the bony segment stabilization system 230B further includes at least one bony fixation element retention module 400. The bony fixation element retention module 400 may engage a bony fixation element 40B via an opening or channel 26B in an opening 20B (FIG. 4B). The bony fixation element retention module 400 may include at least one arm 406 (FIG. 6B) where the arm 406 may limit or prevent bony fixation element 40B dislocation from a bony region 222 and may limit or prevent bony fixation element 40B projection beyond a front surface 28B (FIG. 2B) of the elongated element 10B.

Figure 2A:
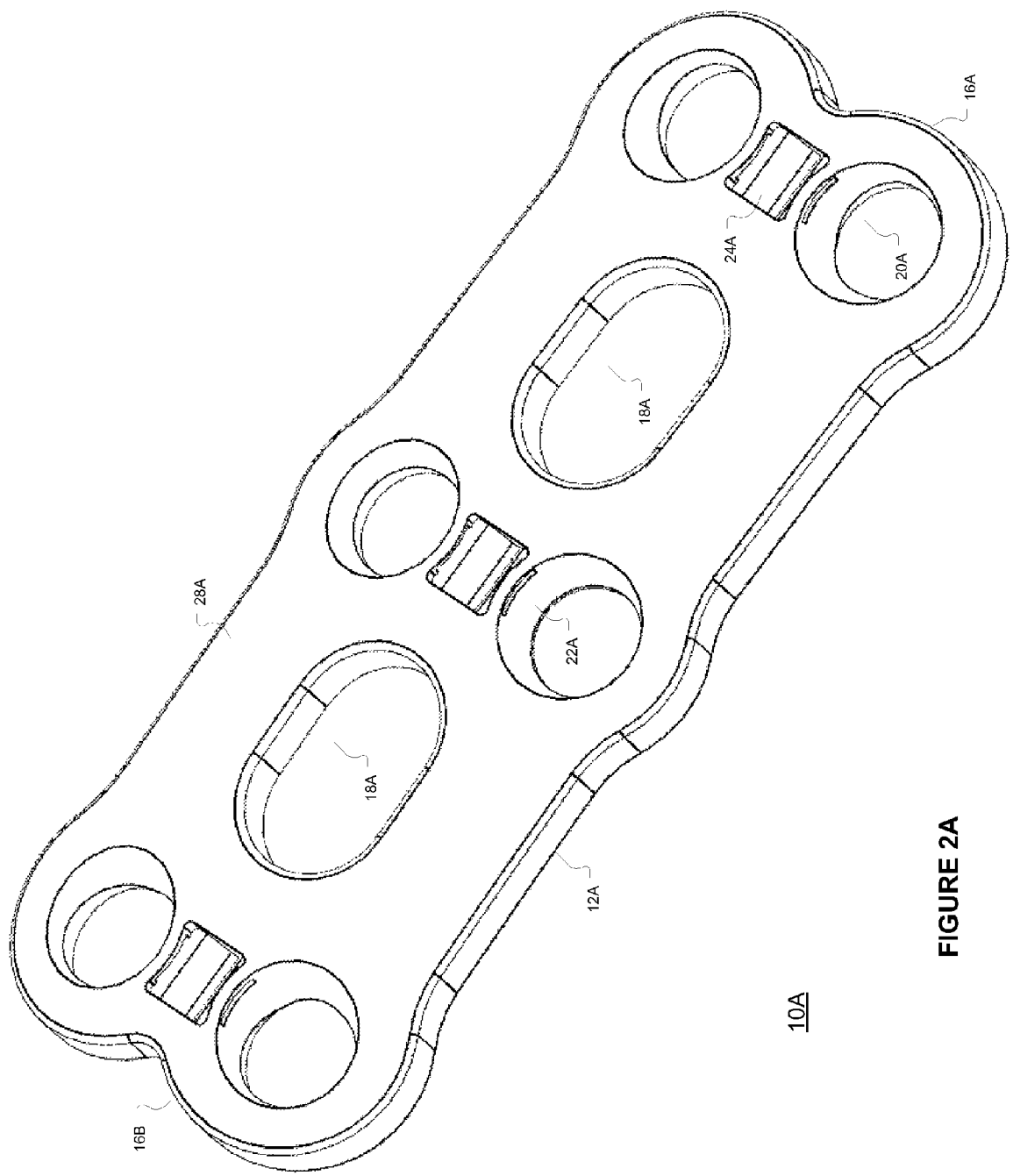
FIG. 2A is a simplified, isometric front view of a mammalian bony segment stabilization system elongated element according to various embodiments.
Figure 3A:
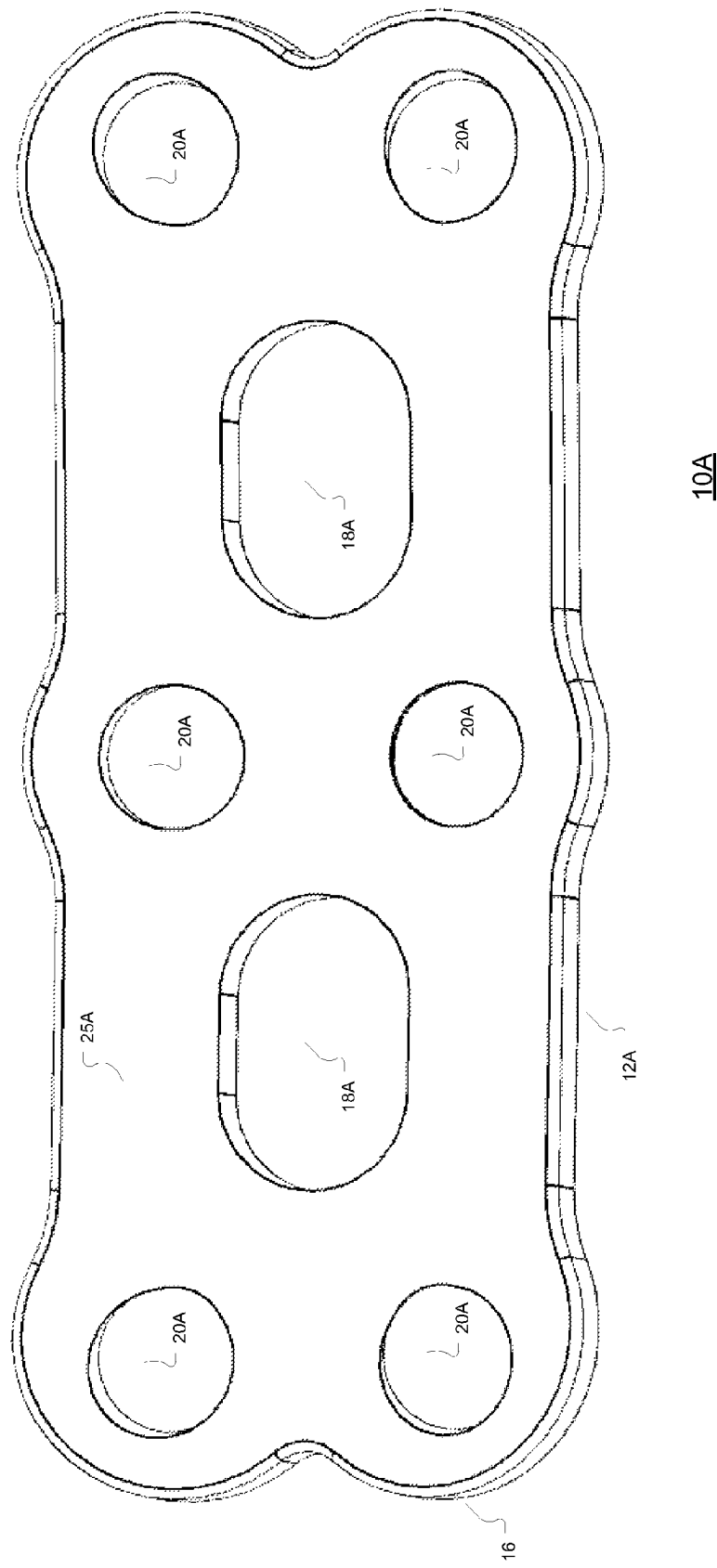
FIG. 3A is a simplified, isometric rear view of a mammalian bony segment stabilization system elongated element according to various embodiments.

FIG. 2A is a simplified, isometric front view and FIG. 3A is a simplified, isometric rear view of the mammalian bony segment stabilization system elongated element 10A according to various embodiments. FIG. 4A is a simplified, isometric front, partial view of a mammalian bony segment stabilization system elongated element bony fixation element coupling 10A segment according to various embodiments. FIG. 5A is a simplified, isometric front, partial view of a mammalian bony segment stabilization system elongated element bony fixation element 10A retention module cavity according to various embodiments. The elongated element 10A includes several bony fixation element openings 20A, implant and region openings 18A, and at least one bony fixation element retention cavity 24A. The elongated element 10A includes a front side 28A, rear side 25A, side portions 12A, a top portion 16B, and a bottom portion 16A.

Figure 9A:
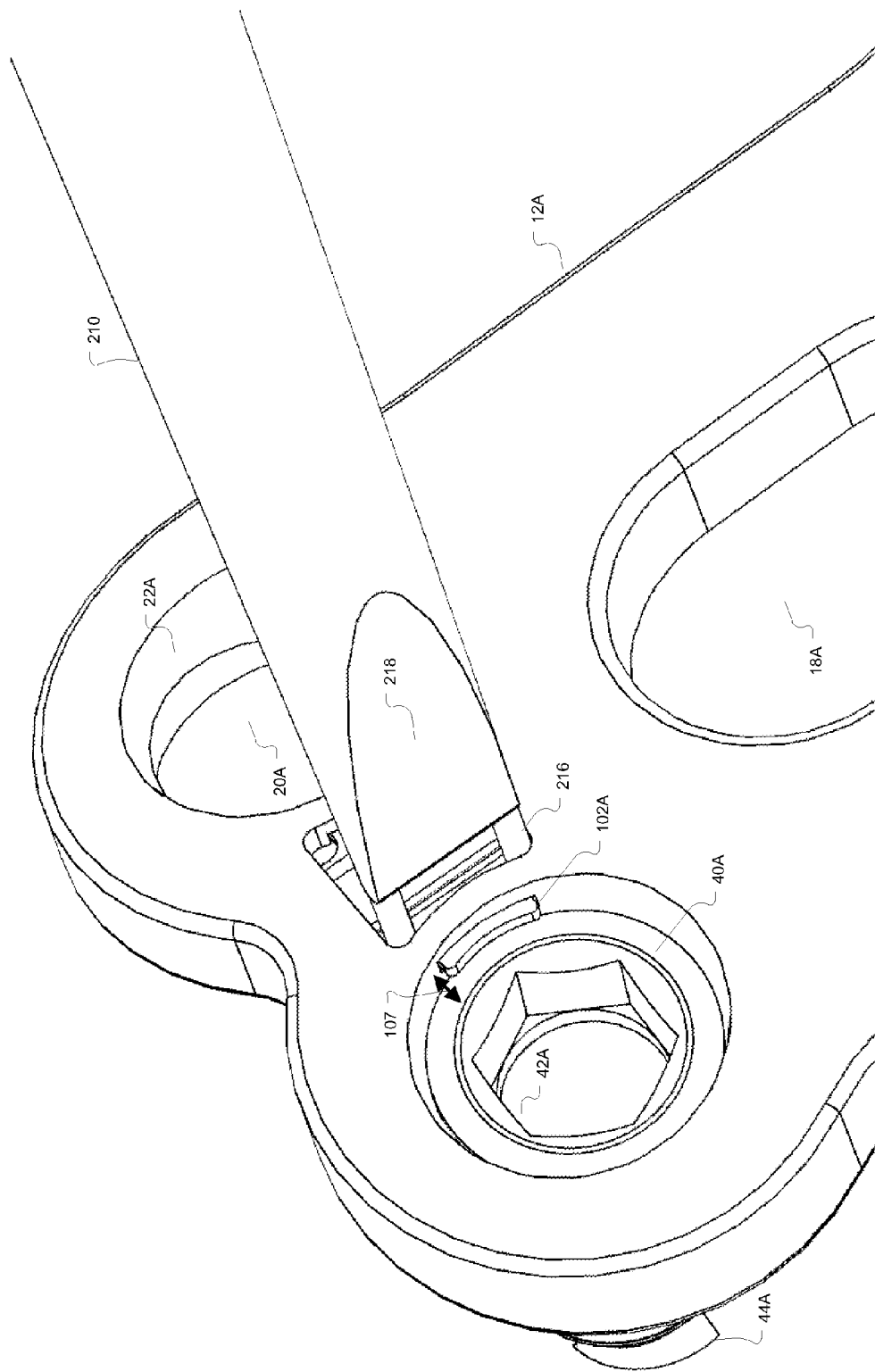
FIG. 9A is a simplified, partial side view of a mammalian bony segment stabilization system including an elongated element, bony fixation element retention module, a bony fixation element, and a bony fixation element retention module deflection pin according to various embodiments.
Figure 9B:
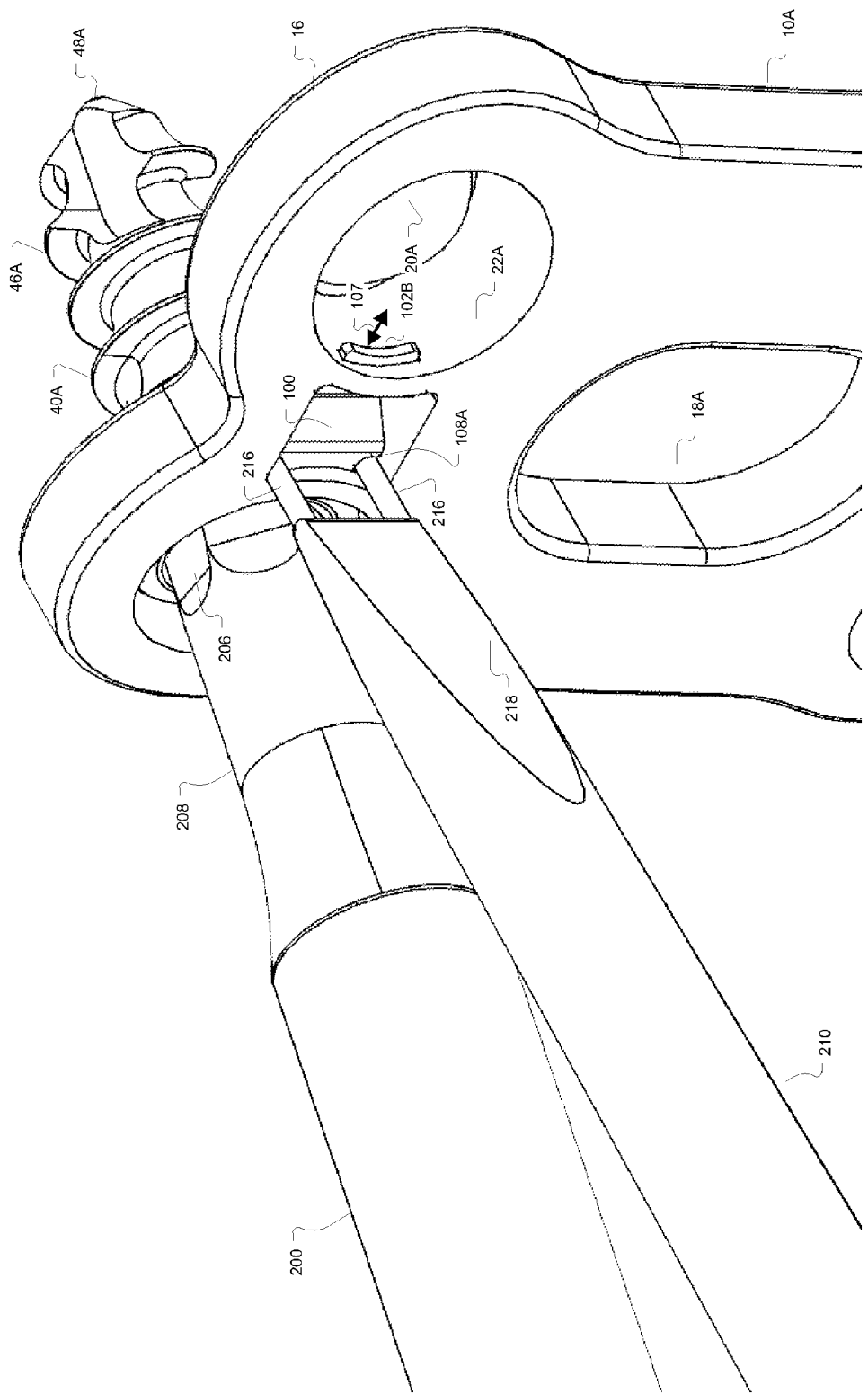
FIG. 9B is a simplified, partial side view of a mammalian bony segment stabilization system including an elongated element, a bony fixation element retention module, a bony fixation element, a bony fixation element retention module deflection pin, and a fixation element driver according to various embodiments.
Figure 9C:
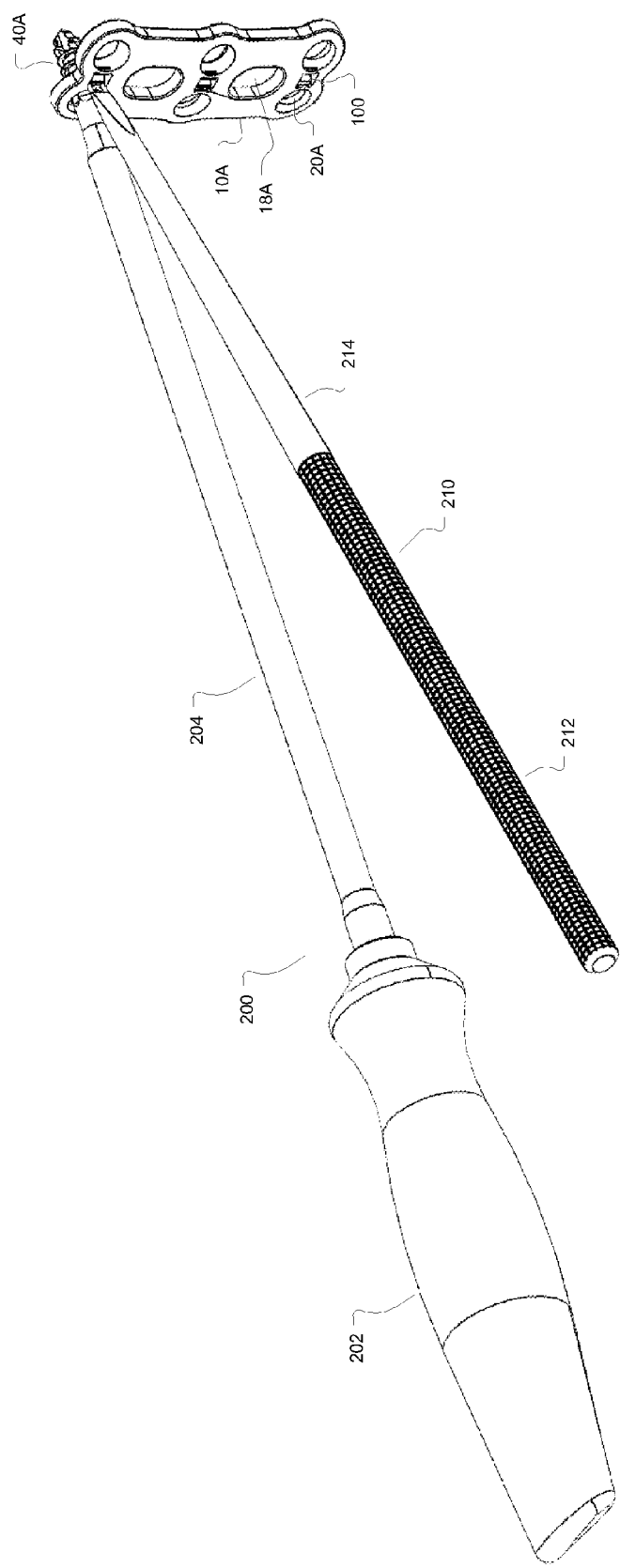
FIG. 9C is a simplified, full side view of a mammalian bony segment stabilization system including an elongated element, bony fixation element retention module, bony fixation element, a bony fixation element retention module deflection pin, and a fixation element driver according to various embodiments.

In an embodiment, the retention module cavity 24A may be configured to hold a bony fixation element retention module (100 in FIG. 6A) in a robustly deformable manner. In an embodiment, each bony fixation element opening 20A may have a sloped or partially spherical wall 22A that may engage an inverse or complementary shape of a bony fixation element 40A head 42A. The opening 20A may include a slot or channel 26A coupling the bony fixation element retention module cavity 24A to the opening 20A. The module cavity 24A may be recessed with a configuration/shape complementary to the bony fixation element retention module 100. The retention module cavity 24A may further include retention module deflection pin access points or sites 32A in one or more corners. One or more pins 216 of a bony fixation element retention module deflection tool 210 (FIG. 10B) may be insertable into the retention module deflection pin access points 32 as shown in FIGS. 9A, 9B, and 9C.

Figure 2B:
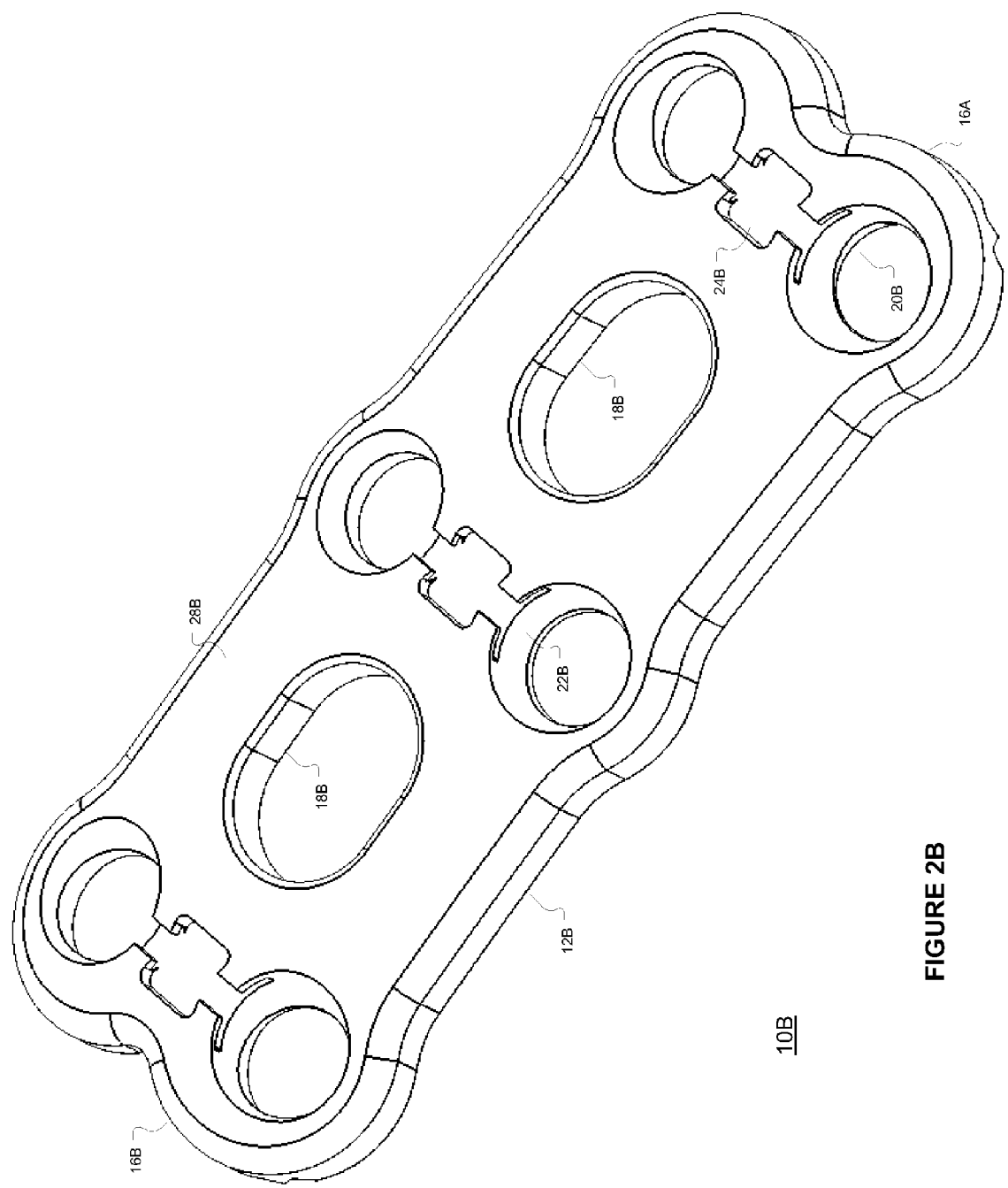
FIG. 2B is a simplified, isometric front view of a mammalian bony segment stabilization system elongated element according to various embodiments.
Figure 3B:
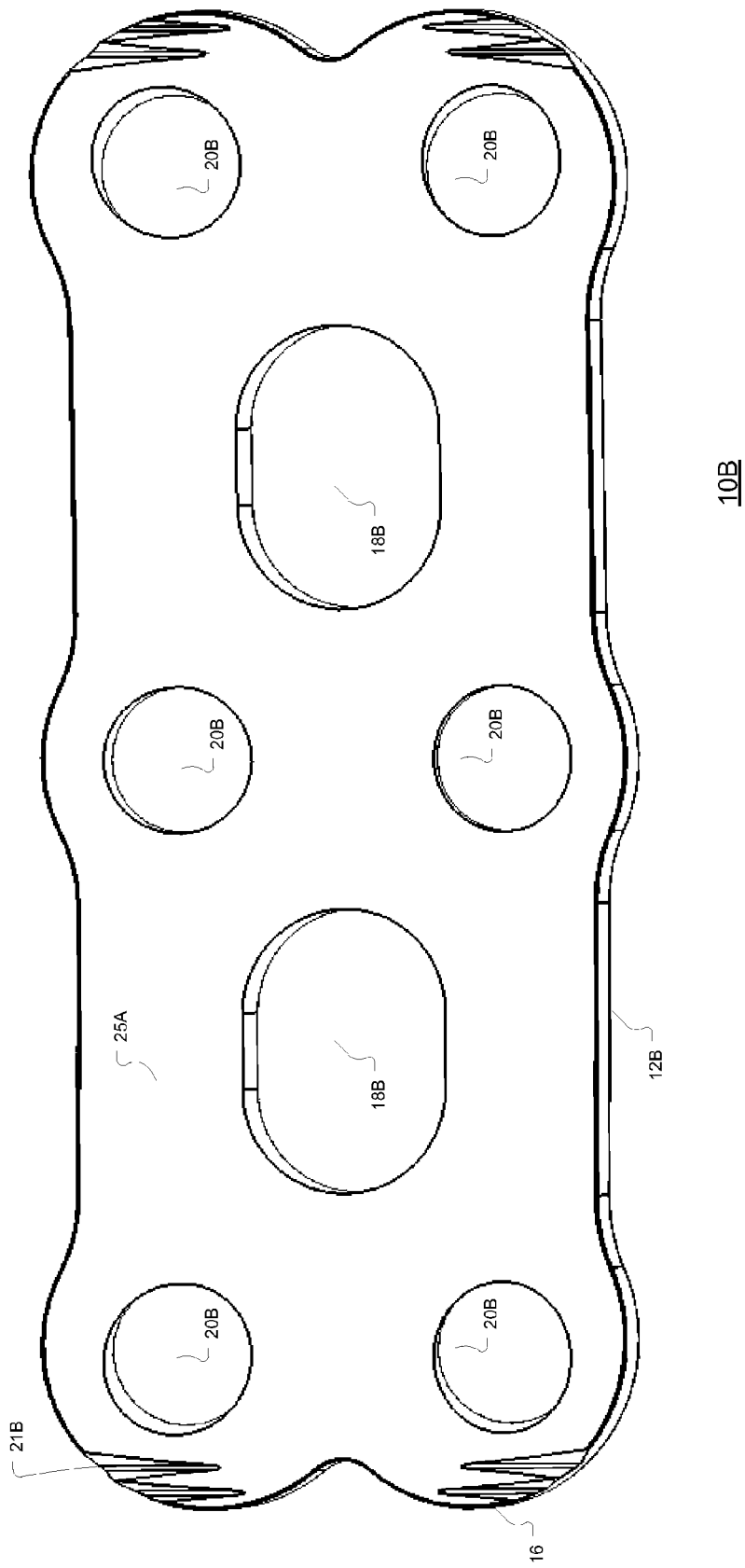
FIG. 3B is a simplified, isometric rear view of a mammalian bony segment stabilization system elongated element according to various embodiments.

FIG. 2B is a simplified, isometric front view and FIG. 3B is a simplified, isometric rear view of the mammalian bony segment stabilization system elongated element 10B according to various embodiments. FIG. 4B is a simplified, isometric front, partial view of a mammalian bony segment stabilization system elongated element bony fixation element coupling 10B segment according to various embodiments. FIG. 5B is a simplified, isometric front, partial view of a mammalian bony segment stabilization system elongated element bony fixation element 10B retention module cavity according to various embodiments. The elongated element 10B includes several bony fixation element openings 20B, implant and region openings 18B, bony interface sections 21B and at least one bony fixation element retention cavity 24B. The elongated element 10B includes a front side 28B, rear side 25B, side portions 12B, a top portion 16B, and a bottom portion 16A.

In an embodiment, the retention module cavity 24B may be configured to hold a bony fixation element retention module (400 in FIG. 6B) in a robustly deformable manner. In an embodiment, each bony fixation element opening 20B may have a sloped or partially spherical wall 22B that may engage an inverse or complementary shape of a bony fixation element 40B head 42B. The opening 20B may include an opening or channel 26B coupling the bony fixation element retention module cavity 24B to the opening 20B including one or more tabs 32B. The module cavity 24B may be recessed with a configuration/shape complementary to the bony fixation element retention module 400. One or more pins 216 of a bony fixation element retention module deflection tool 210 (FIG. 10B) may be insertable into an arm 404A, 404C of the module 400 to releasably deflect an arm 406.

Figure 6A:
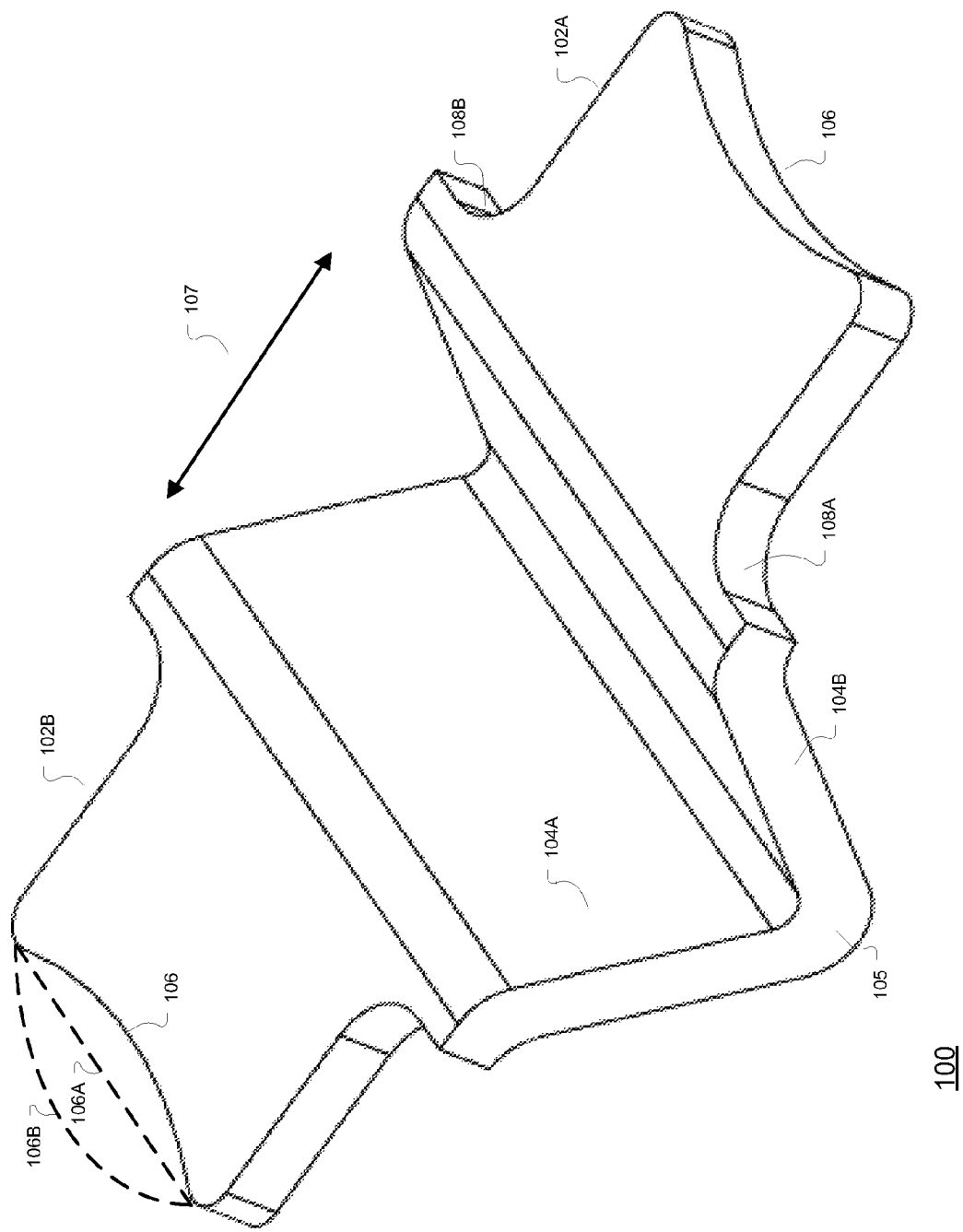
FIG. 6A is a simplified, isometric diagram of a bony fixation element retention module according to various embodiments.

FIG. 6A is a simplified, isometric diagram of a bony fixation element retention module 100 according to various embodiments. The module 100 includes a central axis 105 with two deformable arms 104A, 104B each coupled to bony fixation element retention arm 102A, 102B. Each bony fixation element retention arm 102A, 102B may include a convex 106, flat 106A, or concave 106B end. In an embodiment, a bony fixation element retention arm 102A or 102B may be extended from the cavity 24 through a first slot 26 and the end 106 of the arm 102A, 102B extends into the opening 20. The other bony fixation element retention arm 102A or 102B may be extended from the cavity 24A through the opposite opening or slot 26A. The end 106 of the other arm 102A, 102B may extend into another or opposite opening 20A. The retention module 100 may include insets 108A, 108B where the insets may be engaged by a pin 216 of a bony fixation element retention module deflection tool 210 (FIG. 8). The arms 102A, 102B may move restoratively toward the central axis 105 in the direction shown by 107. The elements 10A, 10B, bony fixation elements 40A, 40B, and retention modules 100, 400 may be formed of any biocompatible material including metallic, ceramic, or polymer materials or a combination of same.

Figure 6B:
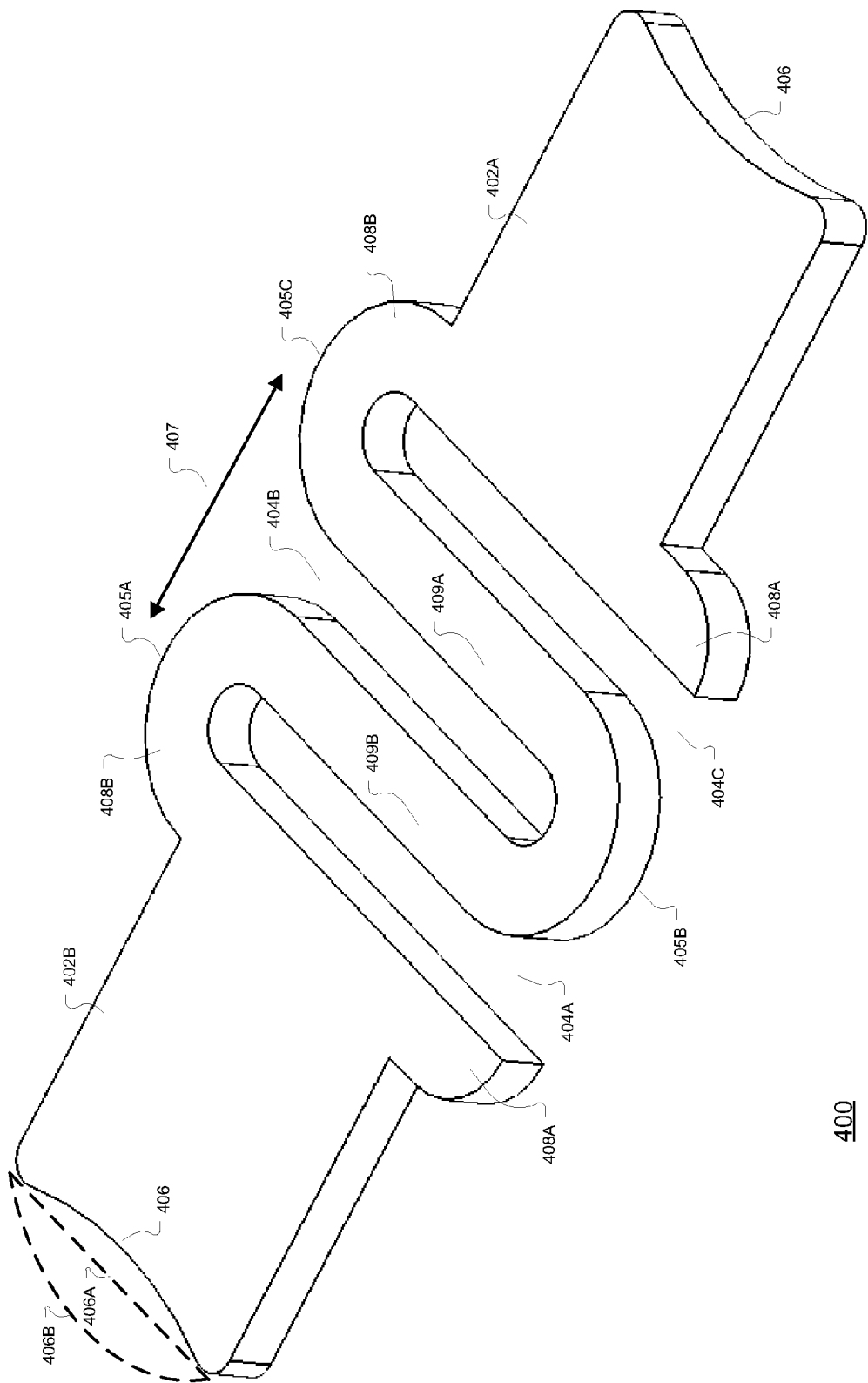
FIG. 6B is a simplified, isometric diagram of a bony fixation element retention module according to various embodiments.

FIG. 6B is a simplified, isometric diagram of another bony fixation element retention module 400 according to various embodiments. The module 400 includes several central arms 409A, 409B and retention arms 402A, 402B coupled by several curved sections 405A, 405B, and 405C. The retention arms 402A, 402B are deformable inwardly in the direction shown by line 407. Each bony fixation element retention arm 402A, 402B may include a convex 406, flat 406A, or concave 406B end. In an embodiment, a bony fixation element retention arm 402A or 402B may be extended from the cavity 24B through a first opening or channel 26B formed by one or more tabs 32B. The arm 402A, 402B ends 406 may extend into an opening 20B.

The other bony fixation element retention arm 402A or 402B may be extended from the cavity 24B through another or opposite opening or channel 26B. The arm 402A, 402B end 406 may extend into another or opposite opening 20B. The retention module 400 may include shoulders 408A, 408B where the shoulders may engage or rest against element 10B tabs 32B. Accordingly, the element 10B tabs 32 may limit the movement of the retention module 400 to prevent expulsion of the module 400 from the cavity 24B during an arm 402A, 402B deformation.

Figure 7A:
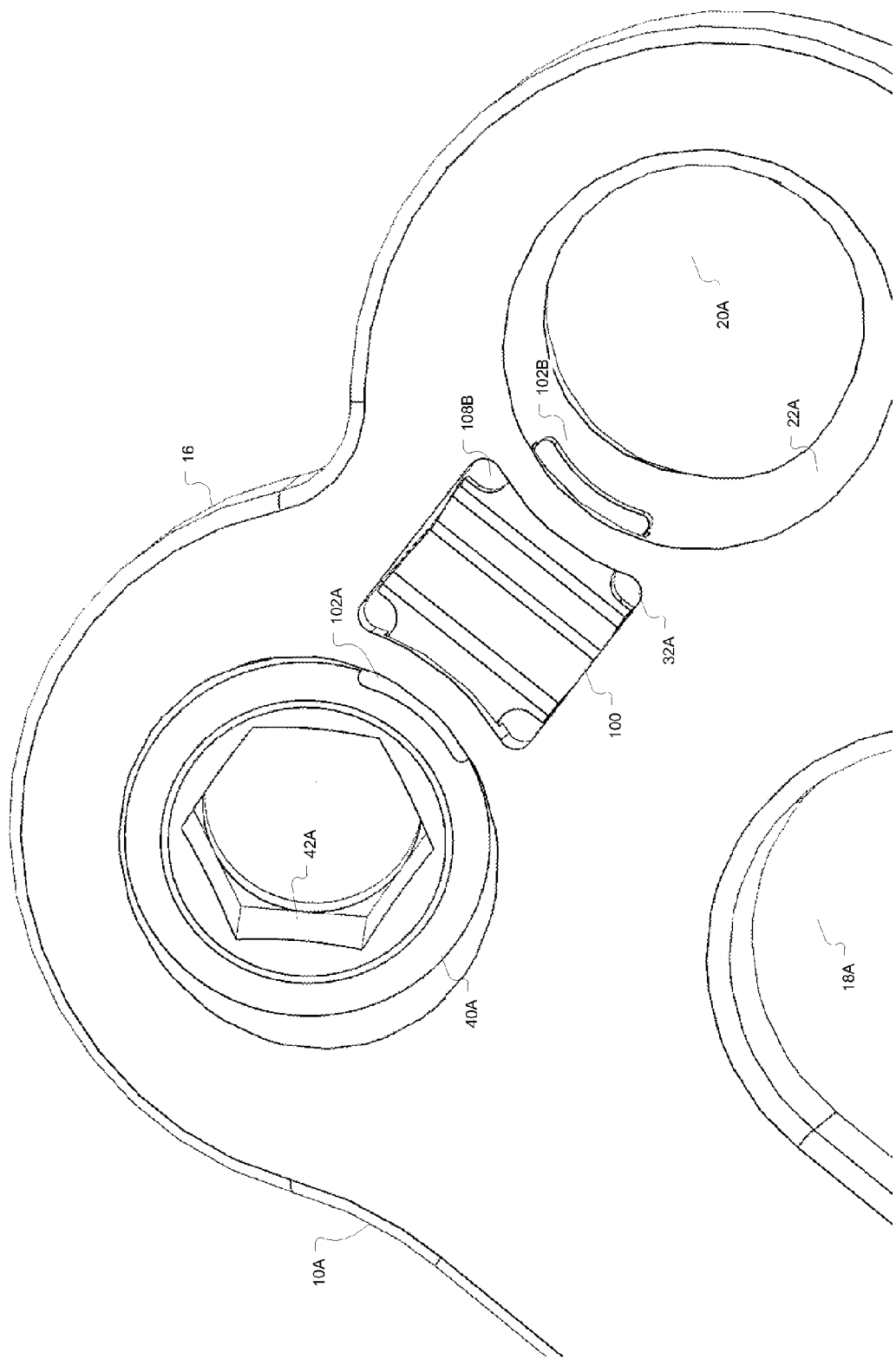
FIG. 7A is a simplified, partial front view of a mammalian bony segment stabilization system including an elongated element, a bony fixation element retention module, and a bony fixation element according to various embodiments.
Figure 8A:
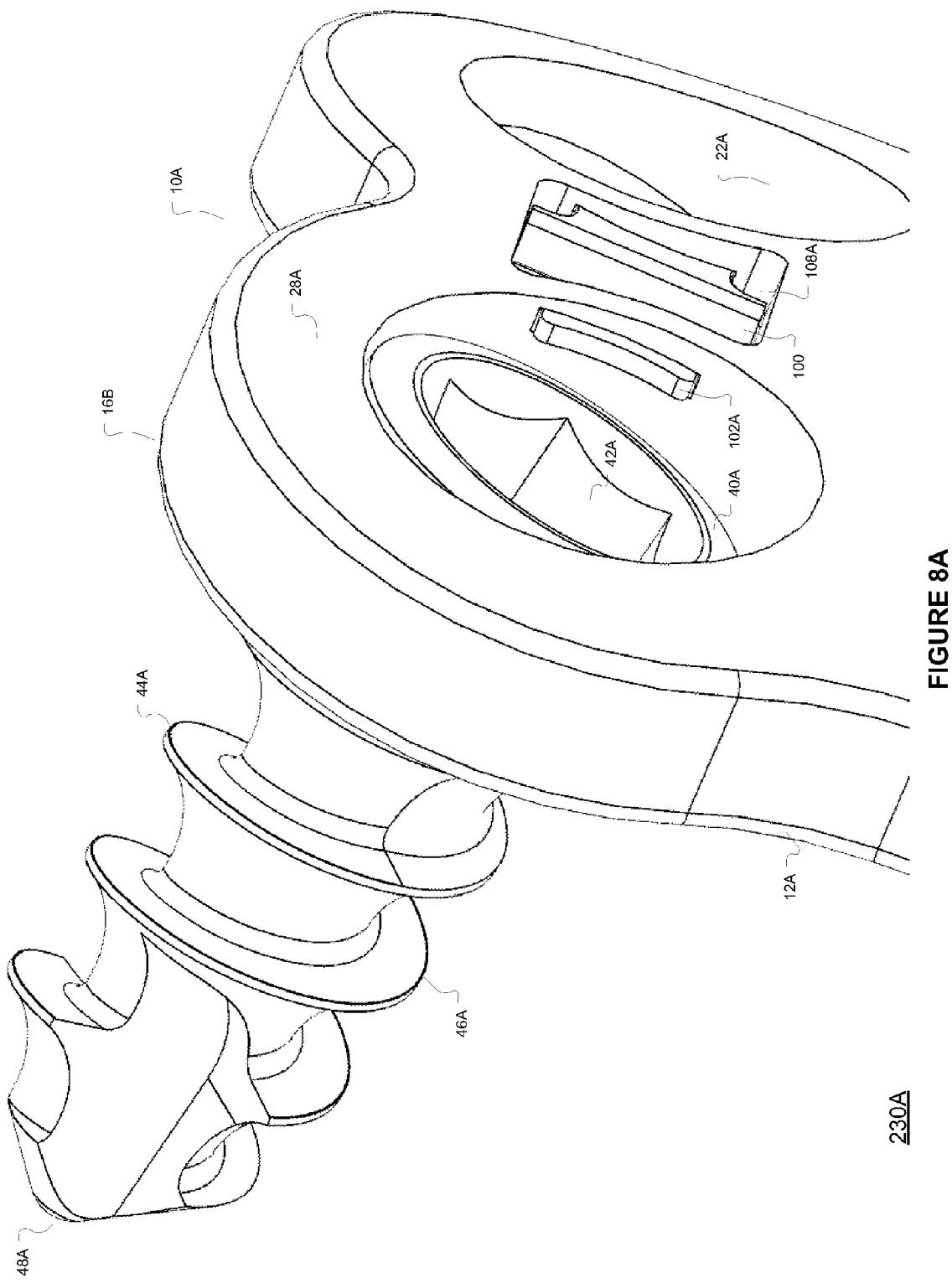
FIG. 8A is a simplified, partial side view of a mammalian bony segment stabilization system including an elongated element, a bony fixation element retention module, and bony fixation element according to various embodiments.

FIG. 7A is a simplified, partial front view and FIG. 8A is a simplified, partial side view of a mammalian bony segment stabilization system 230A including an elongated element 10A, a bony fixation element retention module 100, and bony fixation element 40A according to various embodiments. As shown in FIGS. 7A and 8A the retention module 100 arms 102A and 102B extend into openings 20A and prevent or limit the movement of the bony fixation element 40A and may limit or prevent the bony fixation element 40A head 42A from extending beyond the elongated element 10A front section 28A. The bony fixation element 40A may include a head 42A and a shaft 44A. In an embodiment the shaft 44A may include a tip 48A and a thread 46A. The head 42A may include a tool compatible recess, in an embodiment a female hexagonal recess for a male hexagonal tool (200 of FIG. 10A with male hexagonal tip 206.)

Figure 7B:
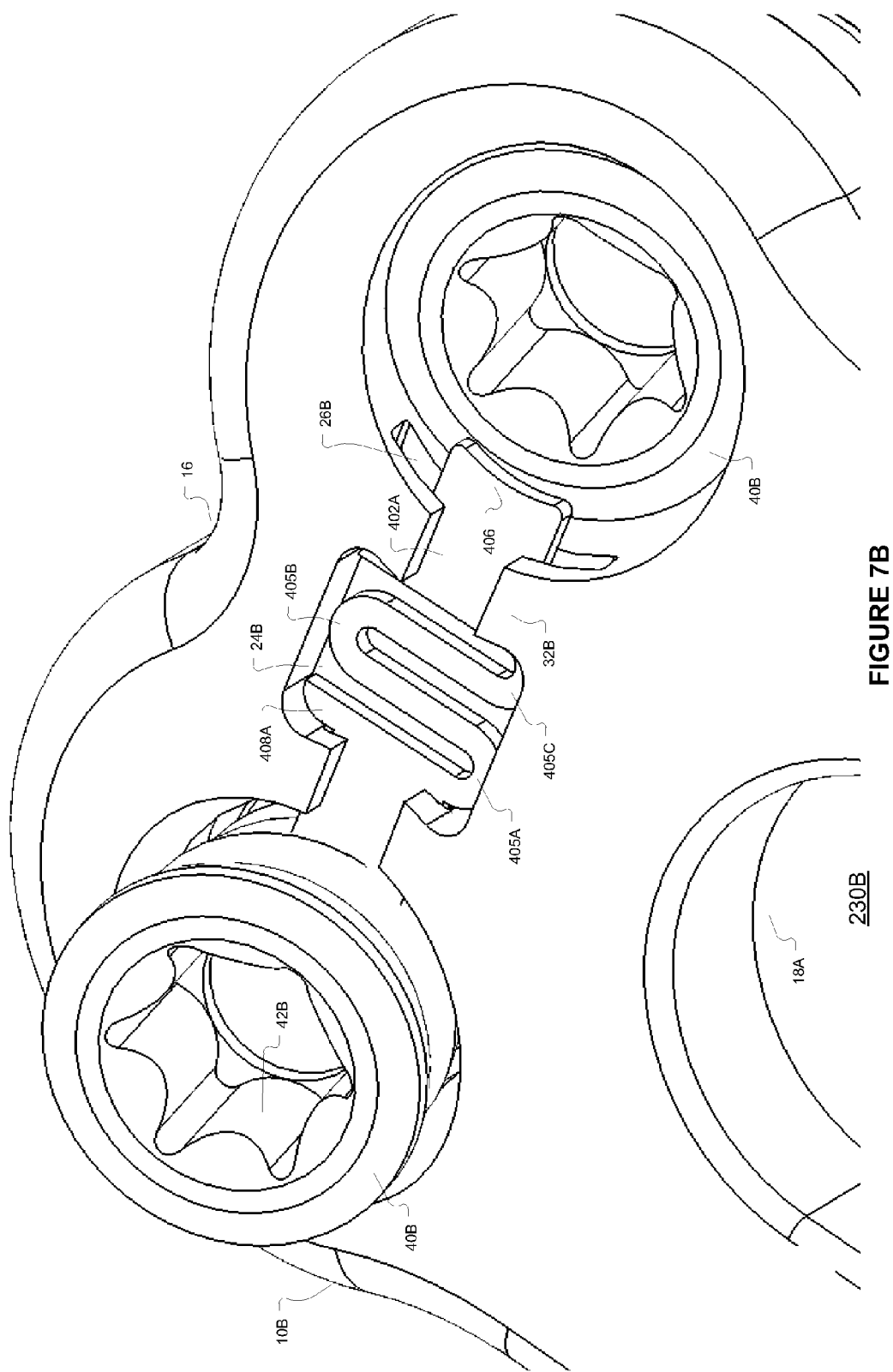
FIG. 7B is a simplified, partial front view of a mammalian bony segment stabilization system including an elongated element, a bony fixation element retention module, and a bony fixation element according to various embodiments.
Figure 8B:
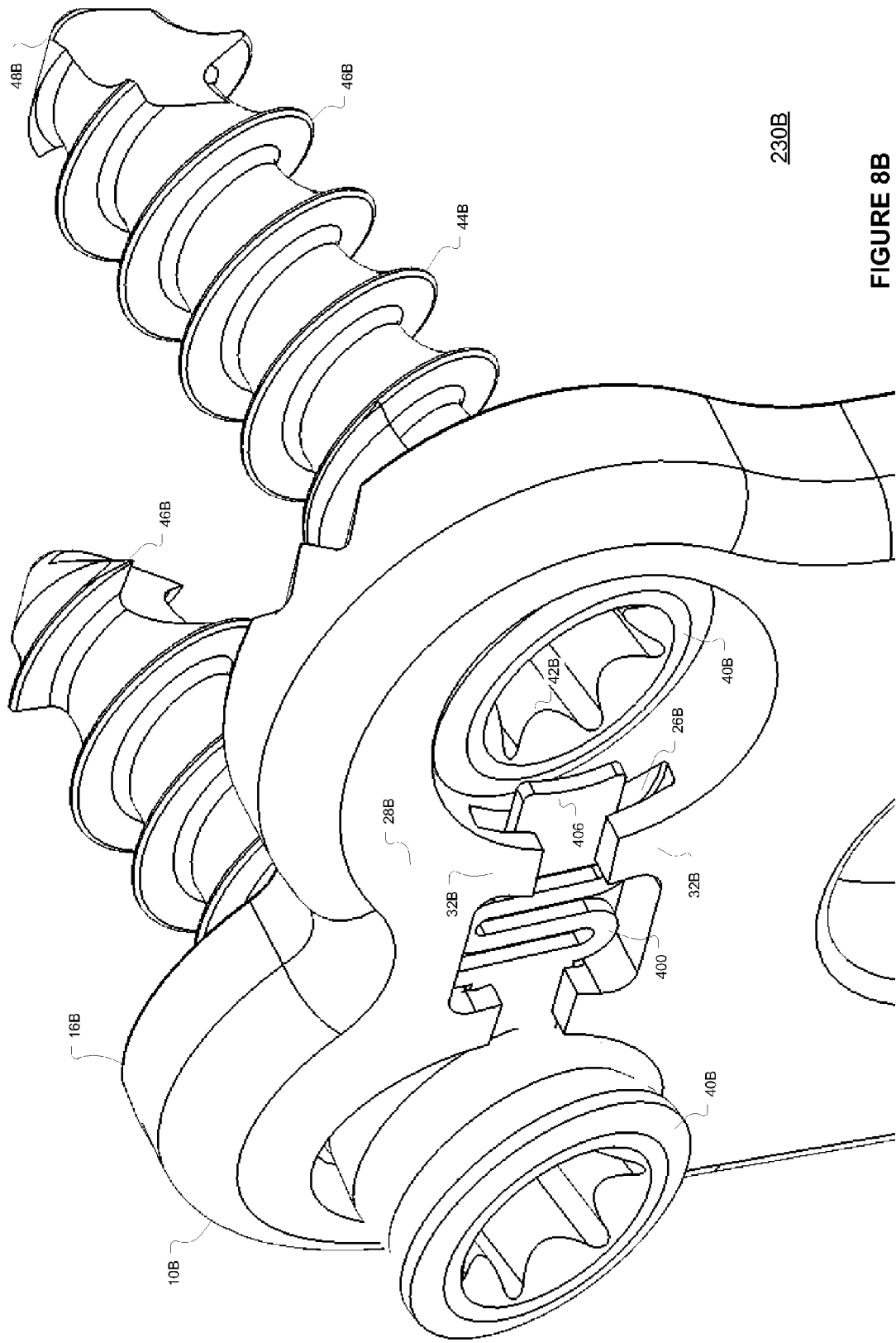
FIG. 8B is a simplified, partial side view of a mammalian bony segment stabilization system including an elongated element, a bony fixation element retention module, and bony fixation element according to various embodiments.

FIG. 7B is a simplified, partial front view and FIG. 8B is a simplified, partial side view of another mammalian bony segment stabilization system 230B including an elongated element 10B, a bony fixation element retention module 400, and bony fixation element 40B according to various embodiments. As shown in FIGS. 7B and 8B the retention module 400 arms 402A and 402B extend into openings 20B and prevent or limit the movement of the bony fixation element 40B and may limit or prevent the bony fixation element 40B head 42B from extending beyond the elongated element 10B front section 28B. The bony fixation element 40B may include a head 42B and a shaft 44B. In an embodiment, the shaft 44B may include a tip 48B and a thread 46B. The head 42B may include a tool compatible recess, in an embodiment a female hexagonal recess for a male hexagonal tool (similar or same as tool 200 of FIG. 10A with male hexagonal tip 206.) As shown in FIGS. 7B and 8B the retention module 400 end 406 extends into the element 10B opening 20B and above a locking element 40B head 42B.

FIG. 9A is a simplified, partial side view of a mammalian bony segment stabilization system 230A including an elongated element 10A, a bony fixation element retention module 100, a bony fixation element 40A, and a bony fixation element retention module deflection pin tool 210A according to various embodiments. In to remove the bony fixation element 40A or 40B, a retention module 100 arm 102A, 400 arm 402A may be reversibly deflected from an opening 20A, 20B toward the module 100 center axis 105, 400 central arms 409A, 409B. The bony fixation element 40A, 40B may then be removed. The retention module 100 arm 102A, 400 arm 402A may be reversibly deflected from the opening 20A, 20B toward the module 100 center axis 105, 400 central arms 409A, 409B in order to employ a bony fixation element 40A, 40B within a bony region through the opening 20A 20B.

FIG. 9B is a simplified, partial side view and FIG. 9C is a simplified, full side view of a mammalian bony segment stabilization system 230A including an elongated element 10A, a bony fixation element retention module 100A, a bony fixation element 40A, a bony fixation element retention module deflection pin tool 210, and a bony fixation element driver 200 according to various embodiments. As shown in FIGS. 9B and 9C, pins 216 of pin tool 210 may engage the recesses 108A of the retention module 100A via the pin access points 32A of the elongated element 10A (sections 404A, 404C of module 400). A bony fixation element driver 200 may include a male head 206 that may engage a female recess of the bony fixation element 40A (40B). The retention module 100 arm 102A (module 400 arm 402A) may be reversibly deflected from the opening 20A (20B) toward the module 100 center axis 105 (400 central arms 409A, 409B) via the pins 216 of the pin tool 210 in order to operate the driver 200 to either insert or remove a bony fixation element 40A (40B) in or from within a bony region 222 through the opening 20A (20B).

Figure 10A:
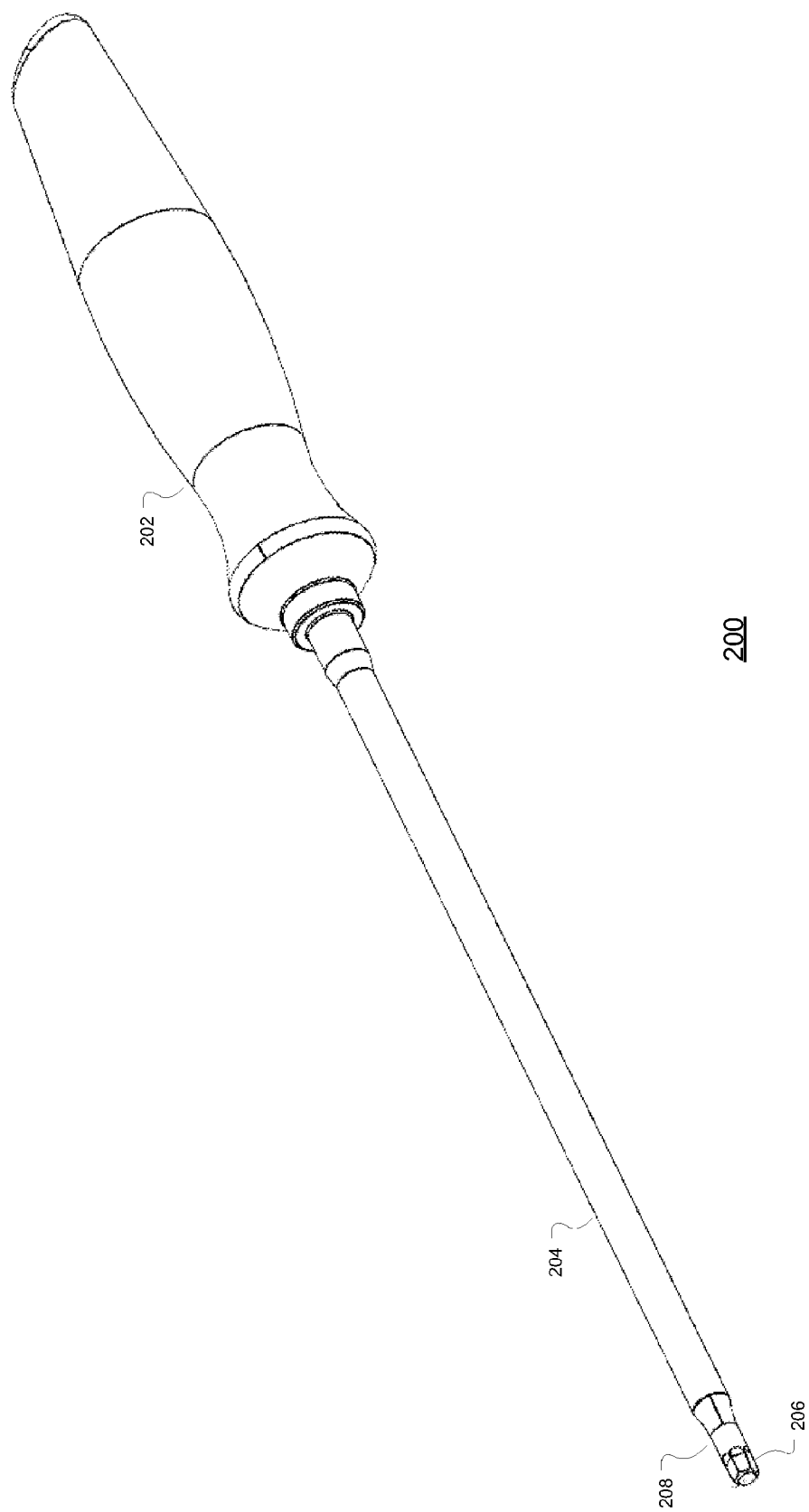
FIG. 10A is a simplified, full side isometric view of a mammalian bony segment stabilization system fixation element driver according to various embodiments.

FIG. 10A is a simplified, full side isometric view of a mammalian bony segment stabilization system fixation element driver 200 according to various embodiments. The driver 200 includes a handle 202, shaft 204, and tip 208. In an embodiment, the tip 208 includes a male hexagonal head 206. The driver 200 may be used to engage a bony fixation element female recess 42A, 42B in order to operate the bony fixation element 40A, 40B. One or more bony fixation elements 40A, 40B may be employed to couple an elongated element 10A, 10B to one or more bony regions 222.

Figure 10B:
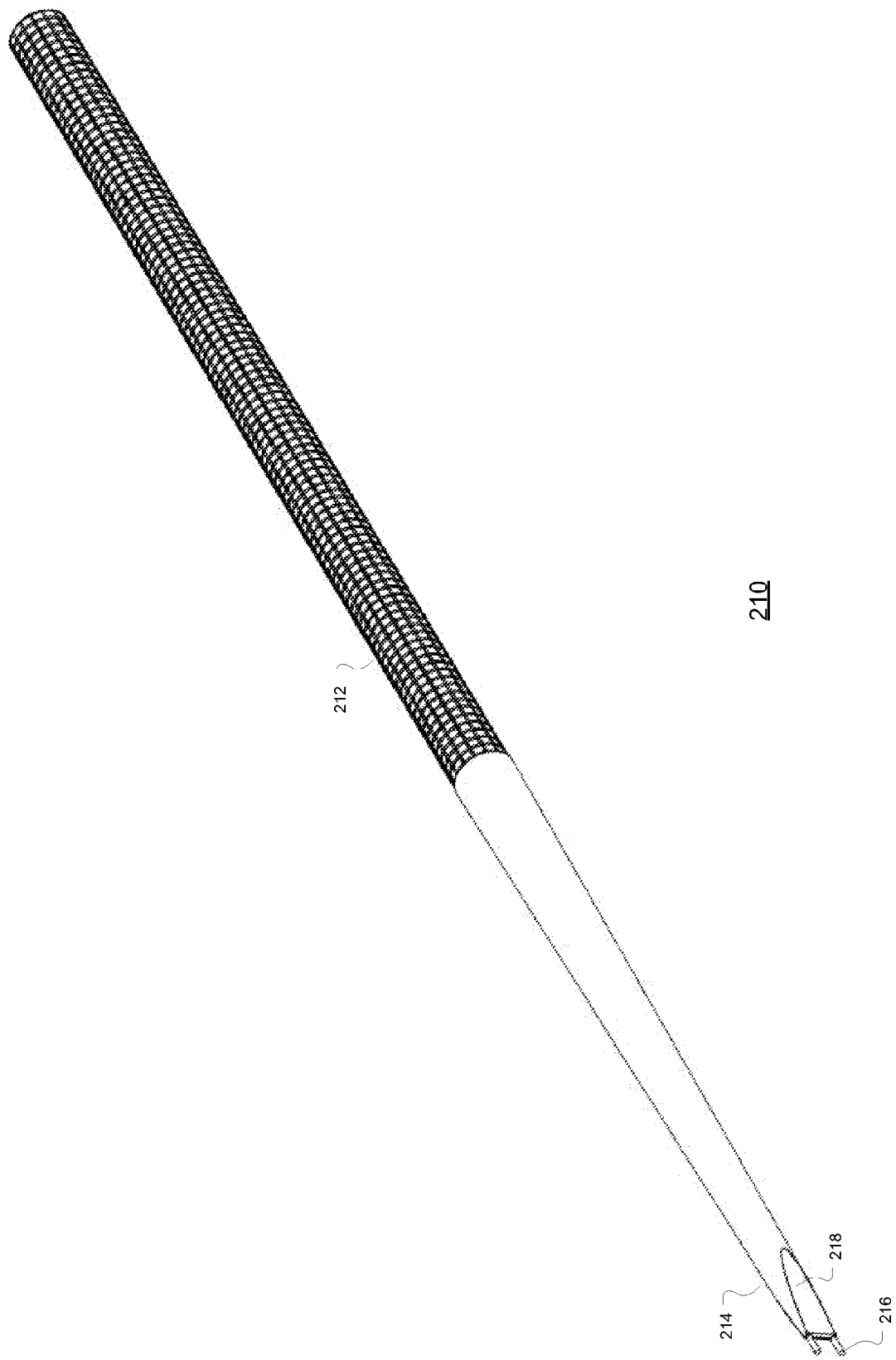
FIG. 10B is a simplified, full side isometric view of a mammalian bony segment stabilization system bony fixation element retention module deflection pin tool according to various embodiments.

FIG. 10B is a simplified, full side isometric view of a mammalian bony segment stabilization system bony fixation element retention module deflection pin tool 210 according to various embodiments. The pin tool 210 may include a handle 212, shaft 214, and a slanted tip 218. The slanted tip 218 may include one or more deflection pins 216. As noted, a retention module 100 arm 102A (400 arm 402A) may be reversibly deflected from an opening 20A (20B) toward the module 100 center axis 105 (400 central arms 409A, 409B) via the pins 216 of the pin tool 210 in order to operate the driver 200 to either insert or remove a bony fixation element 40A, 40B in or from within a bony region 222 through the opening 20A, 20B.

FIG. 11A-11B are flow diagrams illustrating mammalian bony segment stabilization processing algorithms 300 and 320 according to various embodiments. The algorithm 300 may be employed to stabilize one or more bony regions 222. A user such as a surgeon may place an elongated element 10A, 10B having a plurality of openings 20A, 20B over or adjacent to at least one region 222 to be stabilized (activity 302). A user may then create or tap openings in the region 222 corresponding to one or more openings 20A, 20B of the elongated element 10A, 10B. The tapped openings may correspond to the bony fixation element(s) 40A, 40B to be insert through the elongated element 10A, 10B openings 20A, 20B to stabilize the region(s) 222 (activity 304).

A user may then insert the bony fixation driver tool 200 tip 208 into a corresponding segment a bony fixation element 40A, 40B where the bony fixation element 40A, 40B is to be inserted into the tapped opening (activity 306). A user may then drive the bony fixation element 40A, 40B through an opening 20A, 20B of the elongated element 10A, 10B into bony region(s) 222 to be stabilized (activity 308), thereby deflecting an arm 102A, 102B of the retention module 100 (402A, 402B of retention module 400).

A user may continue driving the bony fixation element 40A, 40B through the opening 20A, 20B of the elongated element 10A, 10B into bony region(s) 222 to be stabilized (activity 308), while deflecting the arm 102A, 102B of the retention module 100 (402A, 402B of retention module 400) until a desired torque or depth is obtained (activity 310) or the bony fixation element 40A, 40B head 42A, 42B lies below the elongated element 10A, 10B face 28A, 28B. A user may repeat activities 306, 308, 310 until all the desired bony fixation elements 40A, 40B have been inserted (activity 312).

The algorithm 320 may be employed to remove one or more bony fixation elements 40A, 40B of a mammalian bony segment stabilization system 230A, 230B. A user may then insert one or more pins 216 of a bony retention module deflection tool 210 into a corresponding recess 32A of an elongated element 10A and adjacent a recess 108A, 108B of a retention module 100 where the retention module 100 arms 102A, 102B is located in the elongated element 10A opening 20A occupied by the bony fixation element 40A to be removed (activity 322). In another embodiment, a user may then insert one or more pins 216 of a bony retention module deflection tool 210 into a corresponding recess 404A, 404C of an elongated element 10B of a retention module 400 where the retention module 400 arms 402A, 402B is located in the elongated element 10B opening 20B occupied by the bony fixation element 40B to be removed (activity 322).

A user may then insert the bony fixation driver tool 200 tip 208 into a corresponding segment a bony fixation element 40A, 40B where the bony fixation element 40A, 40B is to be removed from the elongated element 10A, 10B opening 20A, 20B (activity 324). A user may extract the bony fixation element 40A 40B through the opening 20A, 20B of the elongated element 10A, 10B from a bony region(s) 222 while the arm 102A, 102B of the retention module 100 (402A, 402B of retention module 400) is deflected by the deflection tool 210 until the bony fixation element is extracted (activity 326). A user may repeat activities 322, 324, 326 until all the desired bony fixation elements 40A, 40B have been extracted (activity 320).

The accompanying drawings that form a part hereof show, by way of illustration and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In the foregoing Detailed Description, various features are grouped together in a single embodiment for the purpose of streamlining the disclosure. This method of disclosure is not to be interpreted to require more features than are expressly recited in each claim. Rather, inventive subject matter may be found in less than all features of a single disclosed embodiment. Thus the following claims are hereby incorporated into the Detailed Description, with each claim standing on its own as a separate embodiment.

What is claimed is:

1. An apparatus for stabilizing a bony region, comprising:
an elongated element having a long axis, a front and a back, the elongated element defining:
a first opening configured to receive a bony fixation element and extending from the elongate element front to the elongate element back;
a second opening configured to receive another bony fixation element and extending from the elongate element front to the elongate element back; and
a cavity within the elongated element; and
a bony fixation element retention module configured to be securely inserted within the elongated element cavity, the retention module comprising a first arm and a second arm, wherein the first arm is connected to a bias element that deflectably extends the first arm into the first opening and wherein the second arm is connected to the bias element that also deflectably extends the second arm into the second opening when the retention module is securely inserted within the elongated element cavity, the elongate element having a first channel or slot communicating between the first opening and the cavity, and a second channel or slot communicating between the second opening and the cavity, each first and second channel or slot formed under one or more tabs, the retention module first arm deflectably extending from the cavity into the first opening via the first channel or slot, and the retention module second arm deflectably extending from the cavity into the second opening via the second channel or slot, each first and second arm having shoulders that engage the tabs limiting the movement to prevent expulsion of the retention module during arm deformation.

2. The apparatus of claim 1, wherein, in a first position, the retention module first arm limits the protrusion of a bony fixation element inserted in the first opening beyond the elongated element front, and the retention module second arm limits the protrusion of a bony fixation element inserted in the second opening beyond the elongated element front, and in a second deflected position, the first arm permits protrusion of the bony fixation element second arm permits protrusion of the bony fixation element beyond the elongated element front, wherein the first and second arms can separately be placed in the second position independently.

3. The apparatus of claim 2, wherein the bony region includes a vertebral body.

4. The apparatus of claim 1, wherein the bias element is at least an s-shaped spring member formed by several central arms coupled by curved sections to the first and second retention arms.

5. An apparatus for stabilizing a bony region, comprising:
an elongated element having a long axis, a front and a back, the elongated element defining:
a first opening configured to receive a bony fixation element and extending from the elongate element front to the elongate element back;
a second opening configured to receive another bony fixation element and extending from the elongate element front to the elongate element back; and
a cavity within the elongated element; and
a bony fixation element retention module configured to be securely inserted within the elongated element cavity, the retention module comprising a first arm and a second arm, wherein the first arm is connected to a bias element that deflectably extends the first arm into the first opening and wherein the second arm is connected to the bias element that also deflectably extends the second arm into the second opening when the retention module is securely inserted within the elongated element cavity, the elongate element having a first channel or slot communicating between the first opening and the cavity, and a second channel or slot communicating between the second opening and the cavity, each first and second channel or slot formed under one or more tabs, the retention module first arm deflectably extending from the cavity into the first opening via the first channel or slot, and the retention module second arm deflectably extending from the cavity into the second opening via the second channel or slot, each first and second arm having shoulders that engage the tabs limiting the movement to prevent expulsion of the retention module during arm deformation, wherein the bias element is a double s-shaped spring member formed by two central arms and the retention arms spaced by three recesses coupled by curved sections.

* * * * *